(12) United States Patent
Torres et al.

(10) Patent No.: US 9,267,947 B2
(45) Date of Patent: Feb. 23, 2016

(54) **COMPOSITIONS AND METHODS FOR PREVENTING OR TREATING *BURKHOLDERIA* INFECTION**

(75) Inventors: Alfredo G. Torres, Friendswood, TX (US); D. Mark Estes, League City, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 24 days.

(21) Appl. No.: 13/424,341

(22) Filed: Mar. 19, 2012

(65) Prior Publication Data

US 2012/0251565 A1  Oct. 4, 2012

Related U.S. Application Data (60) Provisional application No. 61/516,037, filed on Mar. 28, 2011.

(51) Int. Cl.
| | |
|---|---|
| *C07K 14/195* | (2006.01) |
| *A61P 31/04* | (2006.01) |
| *A61K 39/02* | (2006.01) |
| *A61P 37/04* | (2006.01) |
| *G01N 33/569* | (2006.01) |
| *A61K 39/00* | (2006.01) |

(52) U.S. Cl.
CPC ...... *G01N 33/56911* (2013.01); *A61K 39/0208* (2013.01); *C07K 14/195* (2013.01); *A61K 2039/543* (2013.01); *A61K 2039/55561* (2013.01); *A61K 2039/55577* (2013.01)

(58) Field of Classification Search
None
See application file for complete search history.

(56) References Cited

U.S. PATENT DOCUMENTS

2010/0055123 A1   3/2010   Harland et al.

OTHER PUBLICATIONS

Greenspan et al. (Nature Biotechnology 7: 936-937, 1999).*
Bowie et al (Science, 1990, 257:1306-1310).*
Colman (Res. Immunology, Jan. 1994, vol. 145, pp. 33-36).*
Ulrich MP et al., 2006, J Clin Microbiol 55:551-559.
Whitlock GC et al., 2007, FEMS Microbiol Lett. 277(2):115-122.
Whitlock GC et al., 2008, Trans R Soc Trop Med Hyg. 102/ Supp. 1: S127-S133.
Whitlock GC et al., 2010, Procedia in Vaccinology 2:71-75.
Burtnick et al., 2011, Infection and Immunity 79(4): 1512-1525.

* cited by examiner

*Primary Examiner* — Robert A Zeman
(74) *Attorney, Agent, or Firm* — Norton Rose Fulbright US LLP (57) ABSTRACT

The present invention provides a protein or a fragment or a variant of said protein, wherein the protein, fragment, or variant is capable of producing a protective immune response in an animal, wherein the immune response is protective against infection by *Burkholderia* species. Also provided is a method of preventing or treating infection in an animal caused by *Burkholderia* species which comprises administering an effective amount of the pharmaceutical composition of the present invention to the animal infected with *Burkholderia* species.

6 Claims, 2 Drawing Sheets

COMPOSITIONS AND METHODS FOR PREVENTING OR TREATING *BURKHOLDERIA* INFECTION

This application claims priority to U.S. Provisional Patent application Ser. No. 61/516,037 filed Mar. 28, 2011, which is incorporated herein by reference in its entirety.

STATEMENT REGARDING FEDERALLY FUNDED RESEARCH

This invention was produced in part using funds obtained through a federal grant under No. AI057156 from the National Institutes of Health. Consequently, the federal government has certain rights in this invention.

REFERENCE TO SEQUENCE LISTING

A sequence listing required by 37 CFR 1.821-1.825 is being submitted electronically with this application. The sequence listing is incorporated herein by reference.

BACKGROUND

The present invention relates generally to the fields of microbiology, bacteriology and molecular biology. More specifically, the present invention relates to compositions and methods for preventing or treating infection in an animal caused by *Burkholderia* species.

*Burkholderia mallei* are non-motile bacterium responsible for glanders. This disease mainly affects horses, which are considered to be the natural reservoir for infection, although mules and donkeys are also susceptible (Neubauer et al. 2005 Journal of Veterinary Medicine Series B 52:201-5). Humans are accidental hosts of *B. mallei* following prolonged and close contact with infected animals. *B. mallei* infect humans by entering through open wounds and surfaces of the eyes or nose. Symptoms of glanders are dependent on the route of infection (Srinivasan et al. 2001 N Engl J Med 345:256-8). *B. pseudomallei* are motile bacteria causing melioidosis (Dance 1991 Clin Microbiol Rev 4:52-60). Melioidosis is a life-threatening disease that is mainly acquired through skin inoculation or pulmonary contamination, although other routes have been documented. This saprophyte inhabitant of soil environments is mainly encountered in Southeast Asia and northern Australia, but is sporadically isolated in subtropical and temperate countries (Stone 2007 Science 317: 1022-24).

Both *Burkholderia* species are highly pathogenic and are classified as such in list B by the Centers for Disease Control and Prevention (Horn 2003 Surgical Infections. 4:281-87). *Burkholderia* infections are difficult to treat with antibiotics and there are several reports that indicate it is feasible to protect against melioidosis, at least in animal models of disease, with non-living vaccines (Nelson et al. 2004 J Med Microbiol 53:1177-82). There has also been some progress in identifying partially protective subunits. Passively administered antisera raised against flagellin, polysaccharide, or conjugates of polysaccharide and flagellin, protect diabetic rats against challenge with *B. pseudomallei* (Brett et al. 1994 Infect Immun. 62:1914-19; Brett and Woods 1996 Infect Immun. 64:2824-28; Bryan et al. 1994 Can J Infect Dis. 5:170-78). However, *B. mallei* are not motile and do not produce flagella. Moreover, the ability of flagellin to induce protection against an aerosol, or intranasal challenge has not been reported. Therefore, flagellin was assessed as a potential candidate for inclusion in a *Burkholderia* vaccine and found unsuitable. In contrast, all of the current evidence indicates that other surface-expressed or secreted proteins are immunogenic and structural similarity exists between the proteins in *B. pseudomallei* and *B. mallei* (Whitlock et al. 2007 FEMS Microbial. Lett. 277:115-22; Whitlock et al. 2008 Transactions of the Royal Society of Tropical Medicine & Hygiene 102 Suppl: S127-33).

The prior art is deficient in compositions and methods to protect animals (e.g., equine animals such as horses, donkeys, and mules as well as humans) against the Gram-negative bacterial pathogens *Burkholderia mallei* and *B. pseudomallei* by generating cross-protective immunity against both pathogens. The present invention fulfills this long-standing need and desire in the art.

SUMMARY

The instant invention discloses *Burkholderia* protective proteins that could be administered in vaccines to generate cross-protective immunity against both *B. mallei* and *B. pseudomallei*. Cross-protection is possible based on the similarities in antigenic composition and mechanisms of protection between these organisms. Development of a single vaccine that stimulates T-cell and antibody responses against melioidosis and glanders-producing bacterial agents is feasible. With cross-protective immunity, it is possible to develop a single vaccine capable of generating protection against both melioidosis and glanders The instant invention is directed to peptides or a fragment or a variant of the protein, wherein the protein, fragment, or variant is capable of producing a protective immune response in an animal, wherein the immune response is protective against infection by *Burkholderia* species.

The present invention is further directed to a pharmaceutical composition comprising the protein, fragment, or variant described herein, wherein the protein, fragment, or variant is capable of producing a protective immune response in an animal, in combination with a pharmaceutically acceptable carrier or excipient.

The instant invention is also directed to a vaccine against the protein, fragment, or variant described herein comprising a peptide homologous to the amino acid sequence of SEQ ID NOS:1-3.

The instant invention is also directed to a method of determining whether a subject is infected by a *Burkholderia* species, comprising the steps of: contacting a sample from a subject with the antibody described herein; and detecting a resulting antibody reaction, wherein a positive reaction indicates the subject is infected with a *Burkholderia* species.

The instant invention is also directed to a serodiagnostic kit for determining whether a subject is infected with a *Burkholderia* species, said kit comprising: (a) the antibody described herein linked to a reporter molecule; (b) a buffer; and (c) a reagent for detection of the reporter molecule.

A method of preventing or treating infection in an animal caused by *Burkholderia* species that comprises administering an effective amount of a protein described herein to the animal infected or at risk of being infected with *Burkholderia* species.

Other and further aspects, features, and advantages of the present invention will be apparent from the following description of the presently preferred embodiments of the invention given for the purpose of disclosure.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen (e.g., three dimensional conformation or modification (e.g., phosphorylation)) that gives rise to a biological response is referred to herein as an "antigenic determinant" or "epitope." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another.

The phrase that a molecule "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988), for a description of immunoassay formats and conditions that can be used to determine specific immunoreactivity. Specific binding between two entities means an affinity of at least $10^6$, $10^7$, $10^8$, $10^9$, or $10^{10}$ M$^{-1}$. Affinities greater than $10^8$M$^{-1}$ are preferred.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated peptide refers to one that can be administered to a subject as an isolated peptide; in other words, the peptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

Moieties of the invention such as polypeptides, peptides, antigens, or immunogens may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The subject will have (e.g., are diagnosed with a *Burkholderia* infection), will be suspected of having, or will be determined to be at risk of developing a *Burkholderia* infection. Compositions of the present invention include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1A: BALB/c mice were challenged i.n. with 2 $LD_{50}$ *B. mallei* 4 weeks following intranasal vaccination with BimA (n=2), BopA (n=5), Combo (n=5), LolC (n=6), Hcp1 (n=8) or Control (n=8). BopA- and SimA-vaccinated animals resulted in 100% survival up to 21 days postchallenge. FIG. 1B: BALB/c mice (n=15; pooled data from 3 separate experiments) were immunized 3 times with the indicated antigens, then challenged i.n. with 2 $LD_{50}$ *B. pseudomallei* strain 1026b and survival times determined.

FIG. 2A: *B. mallei* antibody response post-vaccination. Western blots were performed on sera collected 2 weeks post-boost to determine IgG reactivity. Mice vaccinated with recombinant BopA, BimA, LolC and Hcp1, individually or in combination (combo), demonstrated response to all proteins except LolC. Individually vaccinated mice produced a robust humoral response, although LolC was lacking. FIG. 2B: Isotype-specific responses to the vaccine candidates (IgG1 and IgG2a) detected from vaccinated and challenged mice.

DESCRIPTION

*Burkholderia mallei* and *B. pseudomallei* are gram negative pathogenic bacteria responsible for the diseases glanders and melioidosis, respectively. Furthermore, there is currently no vaccine available against these *Burkholderia* species. The present invention identified protective proteins against these pathogens. Immunization with recombinant *B. mallei* Hcp1 (type VI secreted/structural protein), BimA (autotransporter protein), and BopA (type III secreted protein) generated significant protection against lethal inhaled *B. mallei* ATCC23344 and *B. pseudomallei* 1026b challenge. Immunization with BopA elicited the greatest protective activity, resulting in 100% and 60% survival against *B. mallei* and *B. pseudomallei* challenge, respectively. Moreover, sera from recovered mice demonstrated reactivity with the recombinant proteins. Dendritic cells stimulated with each of the different recombinant proteins showed distinct cytokine patterns. In addition, T cells from immunized mice produced IFN-γ following in vitro re-stimulation. These results indicated therefore that it was possible to elicit cross-protective immunity against both *B. mallei* and *B. pseudomallei* by vaccinating animals with one or more novel recombinant proteins identified in *B. mallei*.

In accordance with the present invention there may be employed conventional molecular biology, microbiology, and recombinant DNA techniques within the skill of the art. Such techniques are explained fully in the literature. See, e.g., Maniatis, Fritsch & Sambrook, Molecular Cloning: A Laboratory Manual (1982); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription and Translation [B. D. Hames & S. J. Higgins eds. (1984)]; Animal Cell Culture [R. I. Freshney, 5 ed. (1986)]; Immobilized Cells And Enzymes [IRL Press, (1986)]; B. Perbal, A Practical Guide To Molecular Cloning (1984).

Therefore, if appearing herein, the following terms shall have the definitions set out below.

A "signal sequence" can be included. This sequence is a signal peptide N-terminal to a target polypeptide that directs the polypeptide to the cell surface or secretes the polypeptide into the media. The signal peptide is typically removed by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more deoxyribonucleotides, preferably more than three. Its exact size will depend upon many factors, which, in turn, depend upon the ultimate function and use of the oligonucleotide.

The term "primer" as used herein refers to an oligonucleotide, whether occurring naturally as in a purified restriction digest or produced synthetically. A "primer" is capable of acting as a point of initiation of synthesis when placed under conditions in which synthesis of a primer extension product, which is complementary to a nucleic acid strand, is induced (i.e., in the presence of nucleotides and an inducing agent such as a DNA polymerase and at a suitable temperature and pH). The primer may be either single-stranded or double-stranded and must be sufficiently long to prime the synthesis of the desired extension product in the presence of the inducing agent. The exact length of the primer will depend upon many factors, including temperature, source of primer and intended use. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two sequences are "substantially homologous" when at least about 75% (preferably at least about 80%, and most preferably at least about 90% or 95%) of the residues match over the defined length of the sequences. Sequences that are substantially homologous can be identified by comparing the sequences using standard software.

The labels most commonly employed for these studies are radioactive elements, enzymes, chemicals that fluoresce when exposed to ultraviolet light, and others. A number of fluorescent materials are known and can be utilized as labels. These include, for example, fluorescein, rhodamine, auramine, Texas Red, AMCA blue and Lucifer Yellow.

Proteins can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}V$, $^{125}I$, $^{131}I$ and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes used in such procedures are known and can be utilized. The preferred are peroxidase, β-glucuronidase; β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

As used herein, the term "host" is meant to include not only prokaryotes but also eukaryotes such as yeast, plant and animal cells. A recombinant DNA molecule or gene which encodes the peptide of SEQ ID NO:2 of the present invention can be used to transform a host using any of the techniques commonly known to those of ordinary skill in the art.

Prokaryotic hosts may include *E. coli, S. typhimurium, Serratia marcescens* and *Bacillus subtilis*. Eukaryotic hosts include yeasts such as *Pichia pastoris*, mammalian cells and insect cells.

The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences that control the termination of transcription and translation. Methods, which are well known to those skilled in the art, can be used to construct expression vectors containing appropriate transcriptional and translational control signals. See for example, the techniques described in Sambrook et al., 1989, Molecular Cloning: A Laboratory Manual (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein that has been separated from at least some of those components that naturally accompany it. Typically, the protein is substantially pure when it is at least 60%, by weight, free from the proteins and other naturally occurring organic molecules with which it is naturally associated in vivo. Preferably, the purity of the preparation is at least 75%, more preferably at least 90%, and most preferably at least 99% by weight. A protein is substantially free of naturally associated components when it is separated from at least some of those contaminants that accompany it in its natural state. Thus, a protein that is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

As used herein the term "fragment" refers to any portion of the given amino acid sequence of a polypeptide or protein that has the same activity as the complete amino acid sequence. Fragments will suitably comprise at least 5 and preferably at least 10 consecutive amino acids from the basic sequence and does include combinations of such fragments. In order to retain activity, fragments will suitably comprise at least one epitopic region. Fragments comprising epitopic regions may be fused together to form a variant.

In the context of the present invention the expression "variant" refers to sequences of amino acids which differ from the base sequence from which they are derived in that one or more amino acids within the sequence are substituted for other amino acids. Amino acid substitutions may be regarded as "conservative" where an amino is replaced with a different amino acid with broadly similar properties. "Non-conservative" substitutions are where amino acids are replaced with amino acids of a different type. Broadly speaking, fewer non-conservative substitutions will be possible without altering the biological activity of the polypeptide. Suitably variants will be greater than 75% identical, preferably at least 80% identical, more preferably at least 85% identical, and most preferably at least 90% identical to the base sequence. Variants included in the description of the present invention are intended to exclude substitutions that result in the variant having a substantially identical sequence to a genomic sequence from another organism.

Identity in this instance can be judged for example using the BLAST program (vs. 2.2.12) found on the world wide web at ncbi.nlm.nih.gov/BLAST/ or the algorithm of Lipman-Pearson, with Ktuple: 2, gap penalty: 4, Gap Length Penalty: 12, standard PAM scoring matrix (Lipman, D. J. and Pearson, W. R., Rapid and Sensitive Protein Similarity Searches, Science, 1985, vol. 227, 1435-1441).

Antibodies or binding fragments thereof may be polyclonal or monoclonal, which may be produced using conventional methods.

For instance, polyclonal antibodies may be generated by immunization of an animal (such as a rabbit, rat, goat, horse, sheep etc.) with immunogenic proteins or immunogenic subunits or fragments thereof, to raise antisera, from which antibodies may be purified.

Monoclonal antibodies may be obtained by fusing spleen cells from an immunized animal with myeloma cells, and selecting hybridoma cells which secrete suitable antibodies.

Antibody binding fragments include F(ab')2, F(ab)2, Fab or Fab' fragments, as well as recombinant antibodies, such as single chain (sc) antibodies FV, VH or VK fragments, but they may also comprise deletion mutants of an antibody sequence. Acronyms used here are well known in the art. They are suitably derived from polyclonal or monoclonal antibodies using conventional methods such as enzymatic digestion with enzymes such as papain or pepsin (to produce Fab and F(ab')2 fragments respectively). Alternatively, they may be generated using conventional recombinant DNA technology.

These antibodies may be conveniently incorporated into any available antibody based assay, which is optimized for the detection of *Burkholderia* species. Similarly the antibodies are also useful for the diagnosis of melioidosis and glanders by incorporating them into serodiagnostic assays. Suitable antibody based assays can be readily determined by person skilled in the art.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Other carriers may include a variety of lymphokines and adjuvants such as CpG, ISCOMS and others.

Means for conjugating a polypeptide to a carrier protein are well known in the art and include glutaraldehyde, m-maleimidobenzoyl-N-hydroxysuccinimide ester, carbodiimide and bis-biazotized benzidine. It is also understood that the peptide may be conjugated to a protein by genetic engineering techniques that are well known in the art.

As is also well known in the art, immunogenicity to a particular immunogen can be enhanced by the use of non-specific stimulators of the immune response known as adjuvants. Exemplary and preferred adjuvants include complete BCG, Detox, RIBI (Immunochem Research Inc.), ISCOMS and aluminum hydroxide adjuvant (Superphos, Biosector).

As used herein the term "complement" is used to define the strand of nucleic acid that will hybridize to the first nucleic acid sequence to form a double stranded molecule under stringent conditions. Stringent conditions are those that allow hybridization between two nucleic acid sequences with a high degree of homology, but preclude hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of formamide in the hybridization mixture.

As used herein, the term "engineered" or "recombinant" cell is intended to refer to a cell into which a recombinant gene, such as a gene encoding an antigen has been introduced. Therefore, engineered cells are distinguishable from naturally occurring cells that do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

Thus, in one embodiment, the present invention provides a protein or a fragment or a variant of said protein, wherein the protein, fragment, or variant is capable of producing a protective immune response in an animal, wherein the immune response is protective against infection by *Burkholderia* species. In a preferred embodiment, the protein is selected from the group of proteins consisting of SimA, Hcp1 and BopA and fragments and variants thereof. Generally, the infection is caused by *B. mallei* or *B. pseudomallei* or *B. cepacia*. In addition to the description of the variant given above, also contemplated is a protein having at least 90% homology or identity to the protein, and even more preferably, having at least 95% homology or identity to the proteins described herein, most notably having the sequence shown in SEQ ID NOS:1-3.

In another embodiment, the present invention provides a pharmaceutical composition comprising a protein, fragment, or variant thereof, wherein the protein, fragment, or variant is capable of producing a protective immune response in an animal, in combination with a pharmaceutically acceptable carrier or excipient. For example, the protein may have at least 90% homology or identity to the protein, and even more preferably, having at least 95% homology or identity to the proteins described herein, most notably having the sequence shown in SEQ ID NOS:1-3. In yet another preferred aspect of this embodiment, the pharmaceutical composition further comprises at least one additional protein, fragment, or variant is capable of producing a protective immune response in an animal that is protective against infection by *Burkholderia* species. Without being limiting, the pharmaceutical composition may comprise protein, fragment, or variant related to SEQ ID NO:1 and one or more of the proteins, fragments, or variants related to SEQ ID NOS:2-3 or any variation of one or more of these proteins, fragments, or variants.

In yet another embodiment, the present invention provides an antibody or a binding fragment thereof which binds specifically to the protein described herein.

In another embodiment, the present invention provides a method for detecting the presence of B. pseudomallei or B. mallei which method comprises contacting a sample suspected of containing B. pseudomallei or B. mallei cells with the antibody described herein, or a binding fragment of said antibody, and detecting binding there between.

In another embodiment, the present invention provides an isolated nucleic acid that encodes the protective protein or protective fragment or protective variant described herein.

In yet another embodiment, the present invention provides a method of preventing or treating infection in an animal caused by Burkholderia species that comprises administering an effective amount of the protein described herein to the animal infected with Burkholderia species.

A person having ordinary skill in this art would readily be able to manipulate the peptides of SEQ ID NOS:1-3 in order to derive slightly different peptides with the same functions and uses as the peptide of SEQ ID NOS:1-3. Accordingly, the present invention also encompasses peptides that are at least 95% homologous or identical to the amino acid sequence of SEQ ID NO: 2. Preferably, the present invention also encompasses peptides that are at least 90% homologous or identical to the amino acid sequence of SEQ ID NOS:1-3, peptides that are at least 85% homologous or identical to the amino acid sequence of SEQ ID NOS:1-3 as well as peptides that are at least 80% homologous or identical to the amino acid sequence shown in SEQ ID NOS:1-3.

In one aspect of this embodiment of the present invention, the peptide may further comprise a label. In one aspect of this embodiment of the present invention, the peptide is chemically synthesized. In one aspect of this embodiment of the present invention, the peptide is produced in a cell. The peptide may further comprise a carrier. Further, the peptide may be conjugated to said carrier. For example, the protein and carrier may be conjugated by glutaraldehyde, m-maleimidobenzoyl-N-hydroxy-succinimide ester, carbodiimide or bis-biazotized benzidine. Representative examples of useful carriers include keyhole limpet hemocyanin (KLH), human serum albumin, a lymphokine, or an adjuvant. Representative examples of useful adjuvants include IL2, IL4, ILB, BCG, Detox, RIBI, ISCOMS, cationic liposome-DNA complex or aluminum hydroxide.

In another embodiment, the present invention provides a serodiagnostic kit for determining whether a subject is infected with a Burkholderia species, said kit comprising: (a) the antibody described herein linked to a reporter molecule; (b) a buffer; and (c) a reagent for detection of the reporter molecule. Representative reporter molecules include those selected from the group consisting of luciferase, horseradish peroxidase, β-galactosidase, and fluorescent labels.

The following examples are given for the purpose of illustrating various embodiments of the invention and are not meant to limit the present invention in any fashion.

EXAMPLE 1

Recombinant Protein Expression and Purification

Bioinformatics analysis of target sequences was used to indicate the presence (or absence) of an N-terminal secretion sequence, transmembrane domains and homology to published crystal structures. The programs used were SignalP v.3.0, TMHMM v.2.0 and PHYRE v.0.2, respectively (Bendt-sen et al. 2004 Journal of Molecular Biology 340:783-95; Krogh et al. 2001 Journal of Molecular Biology 305:567-80; Kelley et al. 2009 Nature Protocols 4:363-71). DNA sequences coding for B. mallei proteins BopA (BMA_A1521; AA 23-512; SEQ ID NO:1), BimA (BMA_A0749; residues 19-265; SEQ ID NO:2), the Hcp1 (BMA_A0742; residues 1-169; SEQ ID NO:3), and the B. pseudomallei protein LolC (BPSL2277; residues 44-266; SEQ ID NO: 4) (Harland et al. 2007 Infection & Immunity 75:4173-80) were cloned into the pET28a (+) expression vector (Novagen). Primers were designed to PCR-amplify and clone the selected sequences in frame with a C-terminal 6× Histidine tag, for all four targets. Expand high fidelity DNA polymerase (Roche) was used to amplify targets from B. mallei ATCC 23344 or B. pseudomallei K96243 genomic DNA. Once ligated into pET28a (+), plasmid DNA was electroporated into Escherichia coli DH5α. Cloned sequences were verified by DNA sequencing, using T7 promoter/terminator oligonucleotide primers.

Target protein expression in E. coli (λDE3) Rosetta was induced by growth in OVERNIGHT EXPRESS instant TB medium (Novagen) for 18-20 hours. Bacterial pellets were lysed using 10 × Cellytic B (Sigma), and 6× His-tagged proteins were purified by $Ni^{2+}$ affinity chromatography. Purified proteins were dialyzed against two changes of 10 mM Hepes/150 mM NaCl, pH 7.4, aliquoted and stored at −80° C. Protein concentrations were determined using the BCA kit (Pierce) using bovine serum albumin (BSA) as a standard, and sample purity assessed by SDS-PAGE.

EXAMPLE 2

Vaccination and Challenge with B. Pseudomallei or B. Mallei

To evaluate the potential of Burkholderia surface expressed or secreted proteins to generate protective immunity, the purified recombinant proteins were used individually or in combination to vaccinate mice via the intranasal (i.n.) route. For immunization of mice against B. mallei challenge, 6-8 week old female BALB/c mice (n=8 per group) were primed with 10 μg of recombinant proteins mixed with adjuvant (12.5 μg of CpG oligodeoxynucleotide (ODN) 2395 (Coley Pharmaceuticals) and mixed with 12.5 μg immune-stimulating complex (ISCOM) AbiSCO 100 (Isconova AB), followed by a 2 week boost of 5 μg recombinant proteins with adjuvant. Four weeks post-boost, animals were infected by intranasal inoculation with 2 $LD_{50}$ of B. mallei ATCC 23344 administered i.n. to anesthetized mice. Control animals were vaccinated with non-specific protein (Bovine Serum Albumin, BSA) and adjuvant. Animals were observed closely following challenge and euthanized immediately when predetermined endpoints were reached and these time points were used to calculate survival times. The Institutional Animal Care and Use Committee at UTMB approved all animal studies.

Figure 1A:
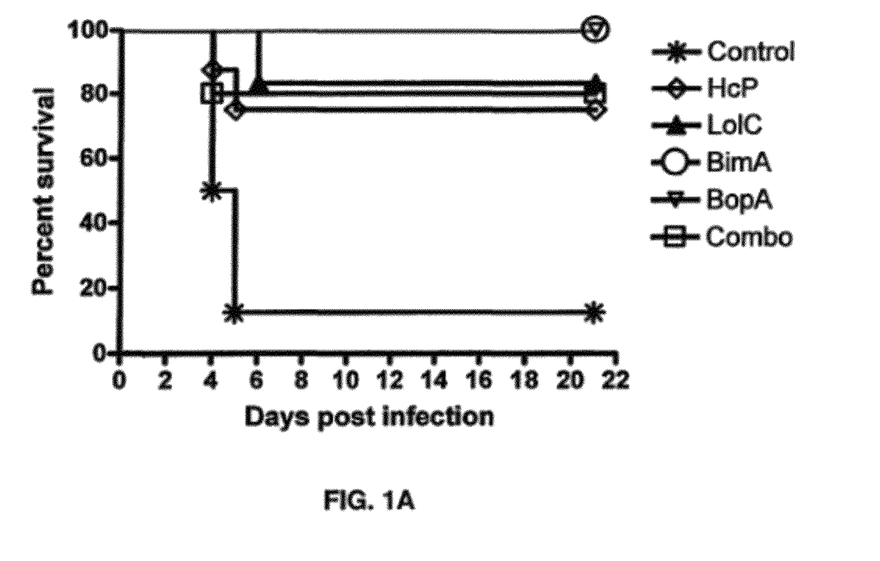
FIGS. 1A-1B show survival of BALB/c mice immunized with different recombinant proteins and challenged with *B. mallei* ATCC 23344 and *B. pseudomallei* 1026b.

Following challenge with B. mallei, 12.5% of control animals survived for >21 days (FIG. 1A). In contrast, survival percentages were significantly increased to 100% up to 21 days post-infection in mice vaccinated with recombinant BimA or BopA. The surviving animals were euthanized at day 21 post-challenge, and the lungs and spleens were homogenized and bacterial counts determined. In all the surviving animals, B. mallei were not recovered from the lungs. However, B. mallei were recovered from the spleens of all surviving animals (data not shown).

Figure 2A:
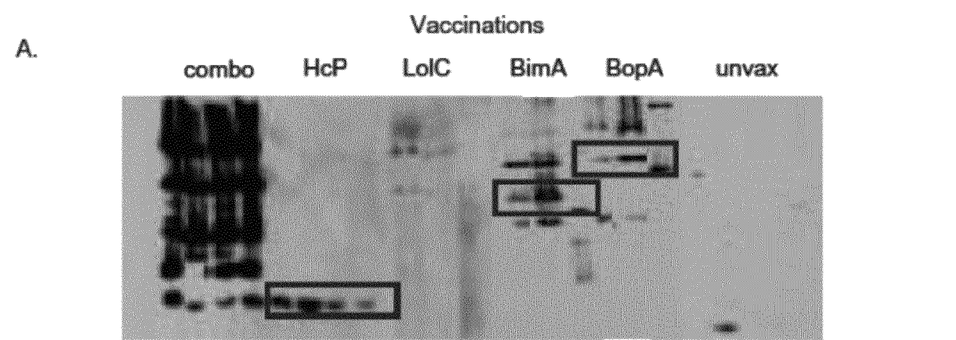
FIGS. 2A-2B show antibody responses.
Figure 2B:
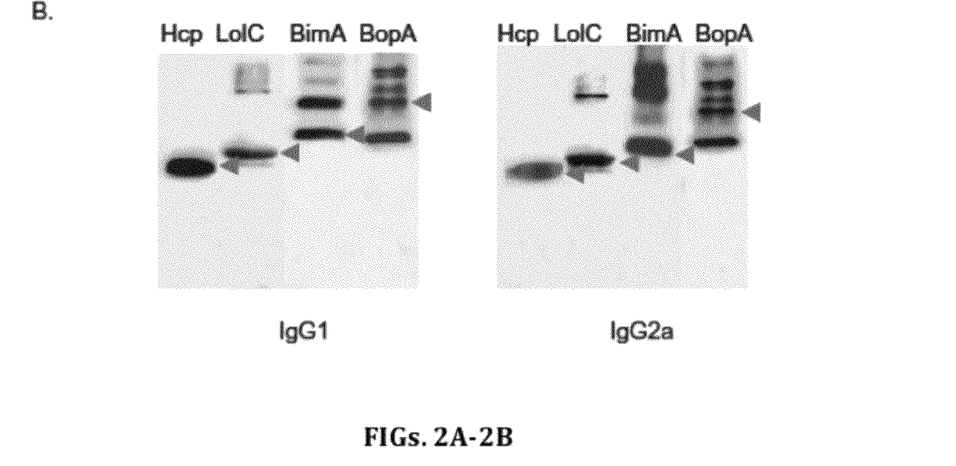

To determine whether antibodies from infected mice reacted with the recombinant Burkholderia proteins, serum was obtained from surviving animals. These sera were then tested for recognition of the purified recombinant Burkholderia antigens Hcp1, BimA, BopA, and LolC by Western blot. Serum from infected mice recognized each of the recombinant antigens tested except for the LolC protein (FIG. 2A) and were recognized by both IgG1 and IgG2a isotypes (FIG. 2B).

Figure 1B:
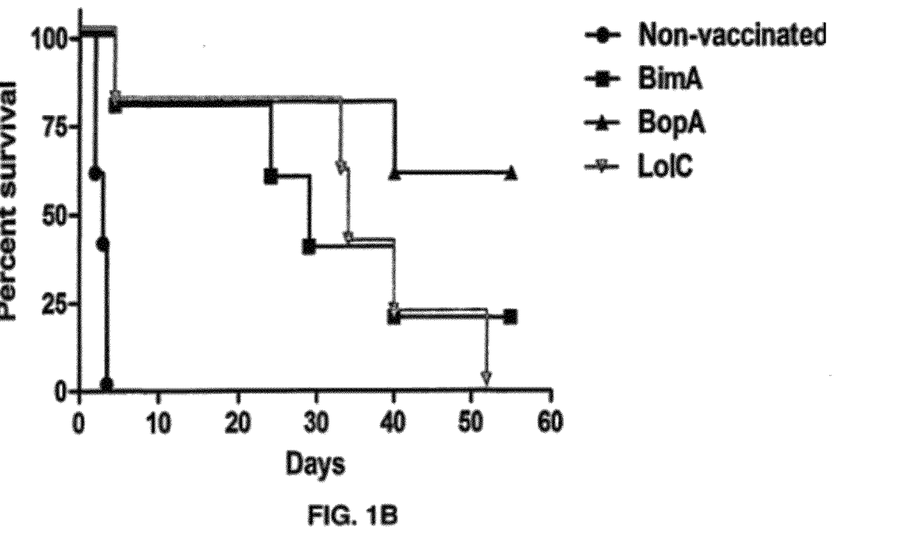

Experiments were also conducted to determine whether the Burkholderia recombinant antigens were also capable of generating protective immunity against B. pseudomallei challenge (FIG. 1B). For these experiments BALB/c mice, (n=5 per group) were primed by i.n. innoculation with two adjuvant systems and immunized with 2 mg of the purified recombinant BimA, or BopA proteins given with CLDC adjuvant (cationic liposome DNA complex), and then boosted 2 weeks later and again 2 weeks after that. The adjuvant used for these studies consisted of cationic liposome-DNA complexes, as reported previously (Zaks et al. 2006 J Immunol. 176:7335-45) for use in non-specific immunotherapy of *B. pseudomallei*. Controls consisted of mice administered cationic liposome DNA complex adjuvant alone, diluent only or BopA antigen alone. Two weeks after the last immunization, mice were subjected to lethal i.n. challenge with 2 $LD_{50}$ of *B. pseudomallei* strain 1026b, as described previously (Goodyear et al. 2009 Infection & Immunity 77:1579-88). Survival times were determined as noted above, and all the *B. pseudomallei* animal challenge studies were approved. The data indicates that the vaccine candidates protected the animals from an initial, acute infection.

Immunization separately or as a combination of each of the four recombinant *Burkholderia* antigens conferred at least 75% protection against *B. mallei* infection at 21 days compared to control mice (FIGS. 1A and 1B). Notably, one of the vaccine antigens (BopA) also conferred significant 60% longer term (>60 days) protection against *B. pseudomallei* challenge. Furthermore, when surviving BopA-vaccinated mice were sacrificed and lung, spleen, and liver tissues plated for detection of *B. pseudomallei*, 25% of the surviving animals were sterile, at least within the limits of detection of the organ culture (typically 50 CFU/organ).

EXAMPLE 3

ELISA Assay for Humoral Responses to Vaccination

Blood was removed from the orbital veins of immunized mice 2 days post-boost. The blood was allowed to clot at room temperature prior to centrifugation at 5,000×g. Serum was collected and stored at −20° C. The recombinant Hcp1-, LolC-, BimA- and BopA-specific protein responses were determined by ELISA (Table 1). Briefly, microtiter plates were coated with 5 mg/ml of the appropriate recombinant protein in PBS overnight. Non-specific binding was blocked using 1% (w/v) ovalbumin in PBS (OVA-PBS) for 1 h at room temperature. The plates were washed three times using 0.05% (v/v) Tween 20 in PBS, and appropriate dilutions of sera in OVA-PBS were added in triplicate and incubated for 2 hours at 37° C. Following the washes, biotinylated-rat-anti-mouse IgG1 or IgG2a (BD Biosciences) diluted in OVA-PBS was added and incubated for 2 hours at 37° C. Next, HRP-conjugated Streptavidin (BD Biosciences) was added and incubated for 25 minutes at room temperature. The substrate ABTS was added and the absorbance at 405 nm was measured. Antibody concentrations (in μg/ml) were calculated from standard curves generated with IgG1 or IgG2a specific antibodies.

TABLE 1

Immune response to Recombinant *Burkholderia* Proteins

| Protein | IgG1 (mg/ml) | IgG2a (mg/ml) |
|---|---|---|
| Hcp1 | 95 | 40 |
| LolC | 0.104 | 0.902 |
| BimA | 2,790 | 5,700 |
| BopA | 2,070 | 6,080 |

The IgG1 and IgG2a responses were analyzed by ELISA using sera removed from immunized and infected mice.

Immunization with recombinant BimA, Hcp1 and BopA proteins provided significant protection against *B. mallei* ATCC 23344 and *B. pseudomallei* 1026b (FIGS. 1A-1B), in which *B. mallei* BopA gave the best results. In addition, the combination of all subunits for protection from *B. mallei* may have utility as a combined vaccine.

The serological results suggest that optimal level of Th1 (IgG2a) and Th2 (IgG1) responses are important for protection in *B. mallei* infection. An interesting observation is that in control group mice, which received only CpG2395 and ISCOM, over 78% survival was observed, whereas in a previous study, mice receiving only ISCOM had −12% survival after infection with 2 $LD_{50}$ of *B. mallei* ATCC 23344, indicating that CpG2395 itself also offers protection (data not shown). There are several reports showing immune-enhancing activity of CpG (Chen 2006 Infection & Immunity 74:1699-705; Elvin et al. 2006 Infection & Immunity 74:1706-11; Krieg 2006 Nature Reviews Drug Discovery 5:471-84; Utaisincharoen et al. 2003 Clinical & Experimental Immunology 132:70-5; Vollmer and Krieg 2009 Advanced Drug Delivery Reviews 61:195-204; Waag et al. 2006 Infection & Immunity 74:1944-8; Wongratanacheewin et al. 2004 Infection & Immunity 72:4494-502). Consistent with this study, a more prolonged time to challenge at 4 weeks to reduce background protection offered by CpG2395 will be used.

Any patents or publications mentioned in this specification are indicative of the level of those skilled in the art to which the invention pertains. These patents and publications are herein incorporated by reference to the same extent as if each individual publication was individually incorporated by reference. One skilled in the art will readily appreciate that the present invention is adapted to carry out the objects and obtain the ends and advantages mentioned, as well as those inherent therein. The present examples along with the methods, procedures, treatments, molecules, and specific compounds described herein are presently representative of preferred embodiments, are examples, and are not intended as limitations on the scope of the invention. Changes therein and other uses will occur to those skilled in the art which are encompassed within the spirit of the invention as defined by the scope of the claims.

The invention claimed is:

1. A method of inducing a protective or therapeutic immune response to *Burkholderia mallei* or *B. pseudomallei* in an animal comprising administering a pharmaceutical composition comprising at least one isolated protein comprising the amino acid sequence of SEQ ID NO:1 or SEQ ID NO:2 and an adjuvant to the animal, wherein an immune response to *Burkholderia mallei* or *B. pseudomallei* is induced.

2. The method of claim 1, wherein the animal is equine.

3. The method of claim 1, wherein the animal is human.

4. The method of claim 1, further comprising administering an isolated protein comprising the amino acid sequence of SEQ ID NO:3.

5. The method of claim 1, wherein the animal is administered an isolated protein comprising the amino acid sequence of SEQ ID NO: 1 and an isolated protein comprising the amino acid sequence of SEQ ID NO:2.

6. The method of claim 5, further comprising administering an isolated protein comprising the amino acid sequence of SEQ ID NO:3.

* * * * *

SEQUENCE LISTING

```
<160> NUMBER OF SEQ ID NOS: 4

<210> SEQ ID NO 1
<211> LENGTH: 490
<212> TYPE: PRT
<213> ORGANISM: Burkholderia mallei
```

```
<400> SEQUENCE: 1

Ala Arg Gly Pro Val Ser Ala Ala Arg Leu Gly Met Lys Glu Arg
1               5                   10                  15

Leu Phe Ala Phe Leu Ala His Val Pro Leu Leu Lys His Cys Asp Ala
            20                  25                  30

Val Arg Arg Tyr Ala Glu Gln Val Arg Met Glu Asn Arg Arg Ser Leu
        35                  40                  45

Glu Val Phe Val Leu Ala Leu Ser Lys Arg Tyr Gly Pro Glu Gly Ala
    50                  55                  60

Lys Ala Ala Phe Asp Tyr Gly Ala Arg Arg Asp Gly Ala Pro Leu Asp
65                  70                  75                  80

Gln Arg Arg Val Arg Asn Met Val Ser Ile Ala Glu His Phe His Gly
                85                  90                  95

Thr Gly Asp Ala Lys Pro Leu Ala Arg Gln Met Val Phe Arg Ser Trp
            100                 105                 110

Glu Cys Arg Gly Leu Asp His Pro Gly His Ala Ser Leu Thr Ile Lys
        115                 120                 125

Asn Gln Ala Asp Ala Asp Ala Gly Arg His Val Tyr Glu His Val Ser
    130                 135                 140

Trp Trp Pro Asn Gln Arg Leu Gly Ser Lys Glu His Phe Asp Arg Ile
145                 150                 155                 160

Glu Pro Lys Thr Leu Asp Gly Tyr Arg Ile Asp Lys Arg Ser Glu Ile
                165                 170                 175

Ser Ser Ala Thr Glu Gln Arg Leu Arg Glu Gly Asp Ala Ala Arg Arg
            180                 185                 190

Lys Ile Leu Ala Asp Gly Phe Lys Tyr Ala Asn Gln Asp Glu Arg His
        195                 200                 205

Asp Ala Leu Phe Phe Pro Arg Ala Gly Gln Lys Leu Asp Lys Asp Ala
    210                 215                 220

Glu Trp Gly Leu Ser Ala Arg Lys Val Tyr Phe Pro Ala Ile Gly Phe
225                 230                 235                 240

Asn His Asp Arg Arg Asp Thr Asp Arg Pro Arg Ala Phe Val Leu Phe
                245                 250                 255

Gly Leu Asn Glu Ala Ala Met Leu Arg Asp Ala Arg Thr Val Lys Glu
            260                 265                 270

Gly Ala Lys Ser Gly Glu Leu Lys Tyr Arg Met Ile Ser Lys Lys Glu
        275                 280                 285

Asn Cys Ala Ser Met Ala Leu Arg Val Leu Arg Ala Gly Gly Ala Glu
    290                 295                 300

His Phe Val Pro Tyr Thr Ala Ala Trp Ile Ser Glu Asp Pro Asn His
305                 310                 315                 320

Ala His Ala Tyr Ala Leu Ala Val Gln Ala Arg Ile Asp Ala Leu Asn
                325                 330                 335

Gln Arg Arg Ala Asp Val Glu Arg Arg Cys Glu Arg Leu Arg Asp Ser
            340                 345                 350

Ala Ser Val Arg Gln Ala Trp Arg Ala Phe Ser Glu Ala Gly Gly Ala
        355                 360                 365

Ser Ala Ser Pro Leu Ala Glu Asp Ala Gly Arg Gly Arg Ala Ser Ala
    370                 375                 380

His Met Arg Gln Ala Arg Leu Asp Glu His Ala Arg Glu Val Glu Arg
385                 390                 395                 400

Ile Gly Ala Tyr Phe Ala Glu Leu Ser Ala Gly Arg Ser Gly Lys His
                405                 410                 415
```

```
Arg Asp Arg Ala Asp Ala Asp Leu Ala Asp Ala Met Lys Arg Cys Ala
                420                 425                 430

Pro Ser Ala Arg Asp Asp Val Ala Ala Leu Thr Arg Lys Ala Ser Val
            435                 440                 445

Leu Val Glu Thr Leu Gly Arg His Leu Asp Ala Pro Pro Pro Ser Asp
        450                 455                 460

Ser Ser Ala Leu Arg Arg Leu Ala Ala His Ala Met Ile Gly Arg Ile
465                 470                 475                 480

Glu Ala Phe Met Ala Ala Ala Ile Ala Ala
                485                 490

<210> SEQ ID NO 2
<211> LENGTH: 355
<212> TYPE: PRT
<213> ORGANISM: Burkholderia mallei

<400> SEQUENCE: 2

Gln Asp Thr Gly Arg Ala Ala Ser Thr Val Pro Phe Gln Arg Phe Ala
1               5                   10                  15

His Leu Leu Cys Ser Ser Ile Ala Pro Leu Ala Leu Gly Phe Ser Thr
            20                  25                  30

Asp Ala Leu Ala Ile Gly Gln Ala Glu Ser Thr Ala Phe Asn Ala Val
        35                  40                  45

Ile Asp Gln Ile Lys Lys Gly Asp Phe Lys Leu Lys Pro Val Gly Asp
    50                  55                  60

Arg Thr Leu Pro Asn Lys Val Pro Pro Pro Pro Pro Pro Pro Pro Pro
65                  70                  75                  80

Pro Pro Pro Pro Pro Pro Pro Pro Ser Pro Pro Pro Pro Pro Ser Pro
                85                  90                  95

Pro Pro Pro Ser Pro Pro Pro Ser Pro Pro Pro Ser Pro Ser Pro Pro
            100                 105                 110

Pro Pro Thr Thr Thr Pro Pro Thr Thr Thr Thr Pro Thr Pro Ser Met
        115                 120                 125

His Pro Ile Gln Pro Thr Gln Leu Pro Ser Ile Pro Asn Ala Thr Pro
    130                 135                 140

Thr Ser Gly Ser Ala Thr Asn Val Thr Ile Asn Phe Asn Ser Thr Gly
145                 150                 155                 160

Ala Ser Ala Met Gly Thr Asn Ser Ile Ala Leu Asp Phe His Ala Arg
                165                 170                 175

Ala Lys Asp Ser Asp Ser Leu Ala Ser Gly Arg Leu Ala His Ala Ser
            180                 185                 190

Gly Pro Arg Ser Thr Ala Ile Gly Ala Glu Asn Ala Ser Gly Gln
        195                 200                 205

Asn Thr Val Ala Leu Gly Ala Gly Ser Ile Ala Asp Arg Asn Asn Thr
    210                 215                 220

Val Ser Val Gly Arg His Gly Asp Glu Arg Gln Ile Val His Val Ala
225                 230                 235                 240

Ala Gly Thr Gln Ala Thr Asp Ala Val Asn Val Gly Gln Leu Asn Leu
                245                 250                 255

Ala Met Ser Asn Ala Asn Ala Tyr Thr Asn Gln Arg Ile Gly Asp Leu
            260                 265                 270

Gln Gln Ser Ile Thr Asp Thr Ala Arg Asp Ala Tyr Ser Gly Val Ala
        275                 280                 285

Ala Ala Thr Ala Leu Thr Met Ile Pro Asp Val Asp Arg Asp Lys Arg
    290                 295                 300
```

```
Val Ser Ile Gly Val Gly Gly Ala Val Tyr Lys Gly His Arg Ala Val
305                 310                 315                 320

Ala Leu Gly Gly Thr Ala Arg Ile Asn Glu Asn Leu Lys Val Arg Ala
            325                 330                 335

Gly Val Ala Met Ser Ala Gly Gly Asn Ala Val Gly Ile Gly Met Ser
            340                 345                 350

Trp Gln Trp
        355

<210> SEQ ID NO 3
<211> LENGTH: 169
<212> TYPE: PRT
<213> ORGANISM: Burkholderia mallei

<400> SEQUENCE: 3

Met Leu Ala Gly Ile Tyr Leu Lys Val Lys Gly Lys Thr Gln Gly Glu
1               5                   10                  15

Ile Lys Gly Ser Val Val Gln Glu Gly His Asp Gly Lys Ile His Ile
            20                  25                  30

Leu Ala Phe Lys Asn Asp Tyr Asp Met Pro Ala Arg Leu Gln Glu Gly
        35                  40                  45

Leu Thr Pro Ala Ala Ala Arg Gly Thr Ile Thr Leu Thr Lys Glu
50                  55                  60

Met Asp Arg Ser Ser Pro Gln Phe Leu Gln Ala Leu Gly Lys Arg Glu
65                  70                  75                  80

Met Met Glu Glu Phe Glu Ile Thr Ile His Arg Pro Lys Thr Asp Thr
                85                  90                  95

Thr Gly Gly Asp Leu Thr Glu Leu Leu Phe Thr Tyr Lys Phe Glu Lys
            100                 105                 110

Val Leu Ile Thr His Met Asp Gln Tyr Ser Pro Thr Pro His Lys Asp
            115                 120                 125

Asp Ser Asn Gly Ile Lys Glu Gly Leu Gly Tyr Ile Glu Glu Ile
        130                 135                 140

Lys Phe Ala Tyr Ser Gly Tyr Ser Leu Glu His Ala Glu Ser Gly Ile
145                 150                 155                 160

Ala Gly Ala Ala Asn Trp Thr Asn Gly
                165

<210> SEQ ID NO 4
<211> LENGTH: 223
<212> TYPE: PRT
<213> ORGANISM: Burkholderia mallei

<400> SEQUENCE: 4

Leu Ile Val Val Leu Ser Val Met Asn Gly Phe Gln Lys Glu Val Arg
1               5                   10                  15

Asp Arg Met Leu Ser Val Leu Ala His Val Glu Ile Phe Ser Pro Thr
            20                  25                  30

Gly Ser Met Pro Asp Trp Gln Leu Thr Ala Lys Glu Ala Arg Leu Asn
        35                  40                  45

Arg Ser Val Ile Gly Ala Ala Pro Tyr Val Asp Ala Gln Ala Leu Leu
50                  55                  60

Thr Arg Gln Asp Ala Val Ser Gly Val Met Leu Arg Gly Val Glu Pro
65                  70                  75                  80

Ser Leu Glu Pro Gln Val Ser Asp Ile Gly Lys Asp Met Lys Ala Gly
                85                  90                  95
```

-continued

```
Ala Leu Thr Ala Leu Ala Pro Gly Gln Phe Gly Ile Val Leu Gly Asn
            100                 105                 110

Ala Leu Ala Gly Asn Leu Gly Val Gly Val Gly Asp Lys Val Thr Leu
            115                 120                 125

Val Ala Pro Glu Gly Thr Ile Thr Pro Ala Gly Met Met Pro Arg Leu
            130                 135                 140

Lys Gln Phe Thr Val Val Gly Ile Phe Glu Ser Gly His Tyr Glu Tyr
145                 150                 155                 160

Asp Ser Thr Leu Ala Met Ile Asp Ile Gln Asp Ala Gln Ala Leu Phe
                165                 170                 175

Arg Leu Pro Ala Pro Thr Gly Val Arg Leu Arg Leu Thr Asp Met Gln
            180                 185                 190

Lys Ala Pro Gln Val Ala Arg Glu Leu Ala His Thr Leu Ser Gly Asp
            195                 200                 205

Leu Tyr Ile Arg Asp Trp Thr Gln Gln Asn Lys Thr Trp Phe Ser
            210                 215                 220
```